United States Patent
Bishara

(10) Patent No.: US 6,571,648 B2
(45) Date of Patent: Jun. 3, 2003

(54) METHOD OF ACCELERATED AGING OF NEAT ASPHALT BINDER USING MICROWAVE RADIATION PROCESS

(75) Inventor: Safwat W. Bishara, Topeka, KS (US)

(73) Assignee: Kansas Department of Transportation, Topeka, KS (US)

( * ) Notice: Subject to any disclaimer, the term of this patent is extended or adjusted under 35 U.S.C. 154(b) by 25 days.

(21) Appl. No.: 09/814,667

(22) Filed: Mar. 22, 2001

(65) Prior Publication Data

US 2002/0157484 A1 Oct. 31, 2002

(51) Int. Cl.$^7$ ................................................. G01N 1/44
(52) U.S. Cl. .................. 73/863.11; 73/865.6; 73/866.4; 374/57
(58) Field of Search ............................... 73/865.6, 863, 73/866.4, 863.11, 863.12, 866; 250/252.1 R, 252.1 A; 374/45, 53, 57; 436/8, 174

(56) References Cited

U.S. PATENT DOCUMENTS

| | | |
|---|---|---|
| 2,070,961 A | 2/1937 | Reeve |
| 2,179,208 A | 11/1939 | Burk et al. |
| 2,317,150 A | 4/1943 | Lovell et al. |
| 3,213,319 A * | 10/1965 | Levy et al. ................. 374/53 |
| 3,499,328 A * | 3/1970 | Kenny et al. ................. 73/866 |
| 4,175,885 A | 11/1979 | Jeppson ..................... 404/77 |
| 4,247,335 A | 1/1981 | Beckham |

(List continued on next page.)

OTHER PUBLICATIONS

Standard Test Method For Effect Of Heat And Air On A Moving Film Of Asphalt (Rolling Thin–Film Oven Test), ASTM Designation D 2872–85 Feb. 1986, pp 311–314.
Standard Specification For Weights And Balances Used In The Testing Of Highway Materials, AASHTO Designation M 231–77 (1982). Month not given (pp. 643–644).
Standard Method For Preparation Of Test Panels For Accelerated And Outdoor Weathering Of Bituminous Coatings, ASTM Designation D 1669–79 Feb. 1980 pp. 471–473.
Standard Specification For Performance Graded Asphalt Binder, AASHTO Designation MPI, Edition 1A, Sep. 1993, Cover Sheet, pp. 1–5.
Standard Method For Preparation Of Test Panels For Accelerated And Outdoor Weathering Of Bituminous Coatings, ASTM Designation D 1669–62 (Reapproved 1968) Month Not Given pp. 526–529.
Standard Practice For Accelerated Aging Of Asphalt Binder Using A Pressurized Acting Vessel (PAV), AASHTO Designation PP1, Edition 1A, Sep. 1993 Cover Sheet pp. 1–8.
Transportation Research Record No. 1488, Unmodified And Modified Asphalt Binders, Transportation Research Board National Research Council, S.W. Bishara and R.L. McReynolds 1995 Month Not Given Cover Sheet pp. 1–12.
Transportation Research Record No. 1535, Characteristics Of Asphalt Binders, Transportation Research Board National Research Council, S.W. Bishara and R.L. McReynolds 1996 Month Not Given Cover Sheet and pp. 98–107.

*Primary Examiner*—Thomas P. Noland
(74) *Attorney, Agent, or Firm*—Chase Law Firm, L.C.

(57) ABSTRACT

An improved method for simulating an oxidative aging of an asphalt sample comprises accumulating a number of samples from the asphalt load under test. The samples are initially heated by convection and microwave units to a common temperature. Subsequently, the samples are incrementally, as heated in a "ramp" control heating, from 27° C. to 147° C. over a 60-minute period. Subsequently, the samples are microwave heated for three successive 60-minute periods and one 30-minute period under a pressure of 440 psi. Upon pressure release, a subsequent short convection heating and subsequent degassing, a resulting aged residue is presented which is equivalent to residue provided by known conventional tests but at a reduced time period.

9 Claims, 1 Drawing Sheet

U.S. PATENT DOCUMENTS

| | | | |
|---|---|---|---|
| 4,252,459 A | 2/1981 | Jeppson | 404/77 |
| 4,252,487 A | 2/1981 | Jeppson | 404/77 |
| 4,319,856 A | 3/1982 | Jeppson | 404/79 |
| 4,594,022 A | 6/1986 | Jeppson | 404/28 |
| 4,619,550 A | 10/1986 | Jeppson | 404/80 |
| 4,849,020 A | 7/1989 | Osborne et al. | 106/281.1 |
| 5,023,187 A * | 6/1991 | Kuebler et al. | 73/823.11 X |
| 5,084,141 A | 1/1992 | Holland | 201/19 |
| 5,279,971 A * | 1/1994 | Schneider | 436/139 |
| 5,289,140 A * | 2/1994 | Jorgenson et al. | 73/863.11 X |
| 5,441,360 A | 8/1995 | Long et al. | 404/77 |
| 5,683,498 A | 11/1997 | Hesp | 106/273.1 |
| 5,895,171 A | 4/1999 | Wiley et al. | 404/77 |
| 5,932,817 A * | 8/1999 | Quentin | 73/863.11 |
| 6,190,917 B1 * | 2/2001 | Barclay et al. | 436/60 |
| 6,207,462 B1 * | 3/2001 | Barclay et al. | 436/155 |
| 6,436,718 B1 * | 8/2002 | Troxler | 73/863.11 X |

* cited by examiner

METHOD OF ACCELERATED AGING OF NEAT ASPHALT BINDER USING MICROWAVE RADIATION PROCESS

BACKGROUND OF THE INVENTION

This invention pertains to method for simulating the oxidative aging of asphalt binders and, more particularly, to an improved accelerated method for simulating an oxidative aging of an asphalt binder by subjecting the binder to pressurized air and elevated temperature produced by microwave radiation.

Asphalt is made from petroleum residues at refineries located throughout the United States. Before a production run of asphalt is released to the purchaser, such as a state highway department, a sample of the asphalt is first tested by the purchaser to assure that it meets certain predetermined specifications. One such test is to evaluate the relative resistance of the asphalt to oxidative aging over an extended period of in-service pavement use. This extended period is preferably five to 10 years of in-service aging in the field. Accordingly, a simulated aging of the asphalt sample must be performed.

A current standard practice for the accelerated aging (oxidation) of an asphalt binder using a pressurized aging vessel ("PAV") is the American Association of State and Transportation Officials ("AASHTO") provisional standard designated PP1, Edition 1A, dated September 1993. In this test, residue from the conduct of a Rolling Thin-Film Oven Test ("RTFOT"), ASTM Designation D2872-85, is used. This RTFOT procedure includes the preheating of an oven for a minimum of 16 hours. The resulting residue is then used in the above-identified PAV test which includes the conductive heating of the RTFOT produced residue for a 20-hour period in a pressurized vessel. During this testing period, the primary asphalt load awaits release at the plant. This resulting backup at the asphalt plant can result in storage problems which may require the asphalt supplier to build and store the production runs of asphalt in EPA-approved storage facilities. Such a procedure obviously results in increased costs for the manufacturer which are in turn passed on to the purchaser.

It is thus desirable to provide a new method for an accelerated aging (oxidation) of the asphalt binder sample which simulates the effects of the RTFOT and PAV tests on asphalt properties but in a much shorter time period. Heretofore it was believed that the heating of an asphalt sample beyond ambient pressure and 115° C. would change the chemistry of the asphalt. Thus, any new method should not introduce any parameters that may affect the asphalt chemistry and the validity of the aging process.

In response thereto I have invented a new method for the accelerated aging of a neat asphalt binder which does not affect the chemistry of the asphalt. My process utilizes a programmable scientific microwave unit (1200 watts at 2450 MHz) capable of housing a series of six asphalt sample vessels on a rotatable turntable. The vessels, each containing a preheated 27° C. sample of the asphalt load, are placed in the microwave unit and first "ramp heated" to increase the sample temperature from 27° C. to 147° C. at 3.08 MPa (440 psi) over a 60-minute period. Subsequently, the samples are microwave heated for three 60-minute periods at a relatively constant 147° C. (±1° C.) at an air pressure of 440 psi. A final microwave 30-minute heating period occurs at a temperature of 147° C. and 440 psi. During these five stages a built in microwave fan is operating at an 80% capacity with the turntable alternately rotating in clockwise and counterclockwise directions so as to evenly distribute the microwave radiation about the samples. The appropriate parameters of interest can then be measured as if the sample has undergone an oxidative aging which occurs in the asphalt binder both during the paving process as well as during five to 10 years of in-service use.

I have found that my method obtains in one procedure a residue that is equivalent to that residue obtained after using the combined "RTFOT+PAV" procedures. (See above note ASTM designation D2872-85, entitled "Standard Test Method for the Effect of Heat and Air on a Moving Film of Asphalt (Rolling Thin-Film Oven Test)" and AASHTO provisional standard entitled "Standard Practice for Accelerated Aging of Asphalt Binder Using a Pressurization Vessel (PAV)" of September 1993.)

Accordingly, it is a general object of my invention to provide an improved method for the accelerated oxidative aging of an asphalt binder by subjecting the sample to pressurized air at an elevated temperature as provided by means of microwave radiation.

Another general object of this invention is to provide in a one-step process an asphalt sample simulative of an oxidative aging that occurs in asphalt both during the paving process as well as during in-service use.

Still another particular object of the invention is to provide a method, as aforesaid, for providing an asphalt sample that is equivalent to samples obtained from the previously used "RTFOT and PAV" methods.

Another object of this invention is to provide an accelerated method, as aforesaid, which simulates the effects of previously known accelerated aging methods of without affecting the chemistry of the asphalt sample.

A further object of this invention is to provide a method, as aforesaid, wherein a higher heating temperature over a shorter period of time at a selected higher pressure is utilized than that used in previous methods while producing a comparable simulated aging of the asphalt sample.

Still another particular object of this invention is to provide a method, as aforesaid, which precludes the introduction of parameters into the asphalt sample which may affect the asphalt chemistry and deleteriously affect the oxidative aging process.

Other objects and advantages of this invention will become apparent from the following description taken in connection with the accompanying drawings, wherein is set forth by way of illustration and example, a now preferred method of this invention.

DESCRIPTION OF THE PREFERRED EMBODIMENT

Figure 1:
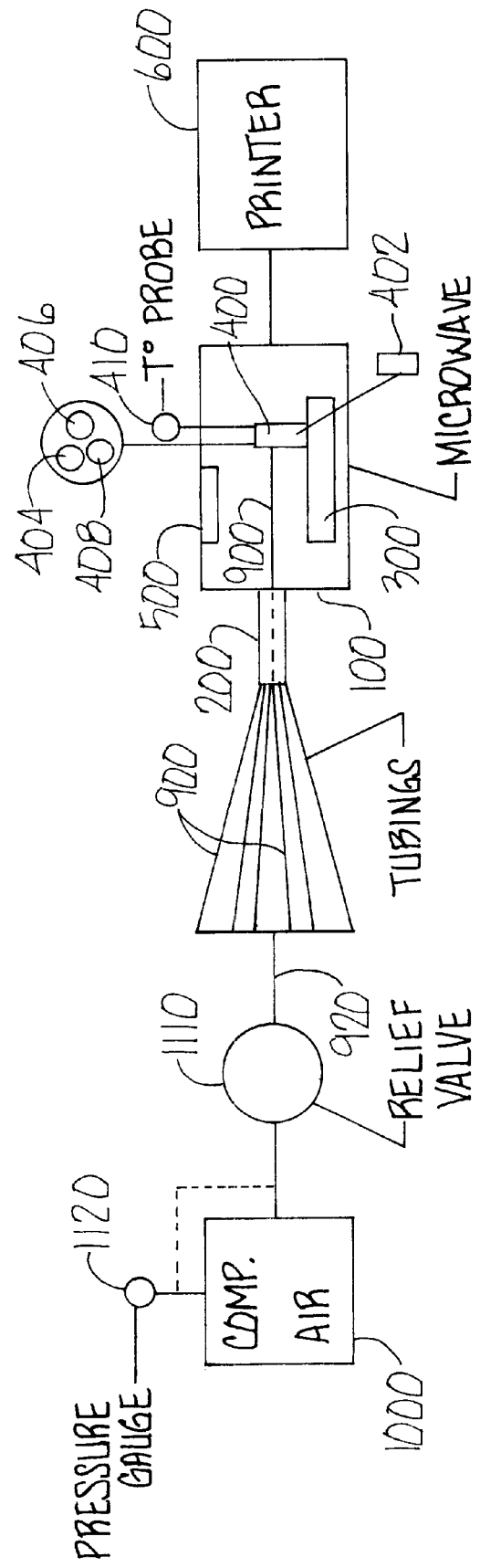
FIG. 1 is a diagrammatic view of the components utilized in the accelerated aging method.

In the performance of my novel method a scientific, microwave-controlled, microwave unit 100, e.g., as a CE Mechanical, MDS2100 unit, is required. The unit must have inlet/outlet ports 200, a rotatable turntable 300, a built in fluoroptic temperature probe 410, a built in mode stirrer or fan 500, and a printer 600. The unit 100 must be programmable to operate via input data as provided by computer software interfacing with the unit as well as delivering output signals, indicative of parameters, e.g., temperature and time, which can be analyzed by such software. The software can control the operation of the power of the unit 100 in 1% increments to control the heating rate.

The microwave unit 100 should have an output power of microwave energy of 1200 watts or higher at a frequency of 2450 MHz at full power. The heating of the microwave unit 100 should be able to be controlled in two modes. A "ramp" temperature mode achieves a desired final temperature over a desired period of time by increasing the temperature from a first temperature to a second temperature in equal increments over the time period. For example, a ramp mode setting will increase the temperature from 0° C. to 120° C.±1° C. over a 60-minute period in increments of 2° C./minute. Alternatively, a "hold" mode is provided at which the desired temperature is held constant, +/−1° C., for a specific period of time. The program software should be able to control the heating of the microwave unit using one or both types of these heat controls per a sample run. It is herein assumed that the microwave unit has a maximum 60-minute period of operation before it must be restarted.

The inlet/outlet ports 200 of the unit 100 allow for the passage of Teflon® tubings 900 therethrough which connect the six sample vessels 400 mounted on the turntable 300 to a compressed air cylinder 1000. The turntable 300 within the unit 100 should be made of a microwave transparent material such as Polypropylene® and have six recesses to hold the six sample vessels 400. The microwave unit 100 should have an alternating turntable 300 drive system such that the table rotates 360° in one direction and then rotates 360° in an opposed direction. The alternate rotations prevent the six pressure tubings 900 and the fluoroptic temperature probe 410 from being entangled and damaged.

The built in fluoroptic temperature probe 410 is insertable into one of the six sample microwave transparent vessels 400 and secured in place by a suitable fastener. As different asphalts heat at different rates, the six sample vessels should all contain the same asphalt material. In the one sample vessel 400 the fluoroptic probe 410 passes through a Pyrex® thermowell. The thermowell protects the probe 410 from contamination by the asphalt material but still provides a means of contact with the asphalt material for sensing the asphalt temperature. The sensed temperature is delivered to the computer software program for constant analysis and printout 600. A mode stirrer or built in fan 500 distributes in various directions the microwave energy produced by the microwave unit 100. The stirrer or fan should have the capability of being set to different speeds from zero to 100%, with 10% increments.

The printer 600 records the time and temperature data of the unit 100 every 30 or 60 seconds. The printer 600 should generate a graph at the end of the sample run to show the variations of the asphalt sample temperature according to time.

The six sample vessels 400 should be able to withstand internal pressure of 4.2Mpa (600 psi) or higher. The samples are placed in liners 402 sample containers which nest within the vessels 400. The liner 402 has approximately a 3.0 cm internal diameter and is 13.0 cm in height. Each liner 402 should also be microwave transparent. Each liner 402 includes a threaded cap of the same material having three openings. One opening 404 is a rupture membrane which acts as a ventilation port for safety. A second opening 406 is a temperature port through which extends the thermowell with the temperature probe 410 therein. As only one temperature probe 410 is used only one of the six vessels 400 has a temperature port with a thermowell. The other cap openings are closed with a nut or the like. A third opening 408 is a port which receives one end of the Teflon® tubing 900 which is in communication with the compressed air cylinder 1000.

The compressed air cylinder 1000 contains a zero grade air, i.e., the moisture and hydrocarbon content is less than three and 1 ppm, respectively. A pressure gauge 1120, 40–1000 psi, is mounted on the compressed air cylinder 1000 and is connected to a metal pressure relief valve 1110 which is connected to the female part of a quick disconnect. The male part of the quick disconnect is connected to the pressure gauge 1120. Teflon® tubings 900, used to connect sample liners 402 to the compressed air cylinder 1000, preferably have a ⅛" outer diameter and a 1/16" internal diameter. The tubings 900 branch from one main line by a system of T-shaped TEFZEL assemblies placed outside the microwave unit. The Teflon® tubing main line 900 is connected through a set of metal flue connectors to a Neptune line 920 (1500 psi, ⅜" diameter hose).

A first thermometer, used for measurement of materials in the zero to 100° C. range, is a non-mercury, partial immersion thermometer that meets or exceeds NIST tolerance for accuracy and can read to 0.01° C. with certainty. For the 100° C. to 170° C. range a mercury partial immersion thermometer which can be read to 0.2° C. with certainty should be used.

A daily calibration of the microwave unit 100 should be carried out to correlate the power setting of the microwave unit 100 with the corresponding output power in watts. One method of calibration may be achieved by filling a 1000-ml flask with distilled water for transfer to a clean, dry 1-L Rubbermaid®, or equivalent, bottle. The container material must be microwave transparent. Using the mercury thermometer, record the temperature of the water to the five-hundredths of a degree on the Celsius scale ($T_1$, ° C.). Upon removal of the turntable from the microwave 100 place the bottle inside the microwave 100. Then heat the water sample for 120 seconds using a 90% power setting and a fan speed of 80%. After heating move the water bottle to a magnetic stirrer and stir vigorously. Then quickly place the thermometer in the water and watch the mercury as it rises to a maximum before dropping. Record the highest temperature ($T_2$, ° C.). This step should be quickly run because the thermometer takes about 30 seconds to reach the maximum temperature. The calculation of the output power absorbed by the water in watts is then made from the equation:

$$P = \frac{(K)(C_p)(m)(\Delta T)}{t}$$

where K=the conversion factor for thermochemical cal.sec$^{-1}$ to Joule.sec$^{-1}$ (Watt) and equals 4.184; $C_p$=specific heat of water in cal.g$^{-1}$.° C.$^{-1}$ and equals 0.9997 at 25° C.; m=mass of water sample in gram (1000 mL≅1000 gram); $\Delta T=(T_2-T_1)$=change in temperature, ° C., due to absorption of microwave energy; and t=time in sec or 120. Substituting in the above equation we get:

$$P=34.86(\Delta T)$$

The above steps are then conducted for 80% and then 70% power settings. The output power P absorbed by the water for each of the settings is then calculated as above.

The absorbed output power in watts is then plotted on the Y-axis versus the percent power setting on the X-axis. A straight line connecting these three points should then be made. Deviations of +/−10 to 15 watts for a single reading are normal and may be expected. Using this straight line calibration curve, select a power setting that generates desired output powers of 850+/− five watts and 1050+/−10 watts.

The pressure gauge 1120 should also be calculated to an accuracy of one percent (1%) at least every six months. This pressure grade is usually calibrated by the manufacturer or a commercial calibration service. Verification of the pressure gauge within the specified requirements should be done periodically by checking against another certified pressure device.

To calibrate the fluoroptic temperature probe 410 fill a 600 ml beaker with distilled water, immerse the temperature probe 410 inside the thermowell and adjacent to it immerse one of the above-described thermometers. The temperature indicated by the thermometer versus that of the fluoroptic temperature probe is recorded. A hot plate and a magnetic stirrer heats and stirs the water. The thermometer temperature when the probe 410 is at room temperature, 45°, 70° and 95° C. is recorded. Upon replacement of the water in the beaker with concentrate sulfuric acid the acid is heated and stirred as above. The temperature of the thermometer when the fluoroptic temperature probe 410 is at 115° C., 135° C. and 155° C. is then recorded. A calibration curve using these two sets of measurements is then plotted. This curve is used to select the temperature of the fluoroptic temperature probe 410 that corresponds to the actual temperature as measured by the thermometer (147° C.).

Once the above calibrations have been achieved the asphalt samples are heated in a convection oven for one hour at 150° C. to bring the samples to a common starting point. A set of six clean sample liners 402 are then heated for four minutes in a household microwave oven to eliminate any traces of moisture. The liners 402 are then placed in a desiccator to cool to room temperature for approximately one hour. In each liner place a weighed 11.0+/−0.1 grams of the asphalt to the nearest 0.01 gram which should yield approximately a 1.0 cm thick layer of asphalt binder. Assemble each vessel 400 with liner 402 therein and caps as above described according to the manufacturer's instructions. Each vessel is then placed on the turntable 300 inside the microwave 100 and connected to the compressed air supply 1100 using the above-described Teflon® tubings 900. The fluoroptic temperature probe 410 is inserted into the opening in the cap associated with one designated vessel 400.

To insure a common starting point for all sample runs inside the microwave 100, the samples are then microwave heated from a room temperature to 27° C. as driven by program software designating a heating temperature of 28° C. for a time of three minutes. The microwave power is programmed at 60% power, i.e. at least 720 watts, with the fan speed being at 30%. The temperature is set one degree higher than the desired temperature of 27° C. to allow for the subsequent cool down resulting from the time lag in the switch from this preheating step to the subsequent microwave treatment. Once the sample temperature reaches 28° C. the program should abort the unit 100 operation.

The microwave unit 100, as programmed, then ages the asphalt material. The software program presents a five-stage treatment process, with stages one to four having 60-minute periods and the fifth stage having a 30-minute period. (Five stages are required as the microwave unit utilized can operate for only a 60-minute period before restart.) An air pressure of 3.08 MPa (440 psi) is delivered to the samples. The fan speed is set at 80%.

In stage one an output power of 850+/−5 watts is used. The "ramp" setting of the unit is used to increase the sample temperature from 27° C. to 147° C. over a period of 60 minutes. In this ramp setting the microwave unit will divide the temperature range of 120° C. over the 60-minute period such that the temperature rises regularly over this period. The percent power setting that corresponds to an output power in the range of 845 to 855 watts as above determined in the microwave power calibration process should be utilized.

In stages two through four an output power of 1050+/−10 watts is used. Each of these stages takes 60 minutes. The temperature is held "constant" at 147° C.+/−1° C. during each period. Again, the exact output power setting is found from the calibration curve as above described. Use the power setting that corresponds to the output power setting in the range of 1040–1060 watts.

The final fifth stage uses the same settings as stages two through four but only for a 30-minute period.

During this microwave treatment the turntable 300 carrying the sample vessels 400 should be observed for regular rotation. A prolonged hesitation at the point of reversal of the rotation of direction, or if the turntable rotates more or less than 360° before reversing rotation direction, indicates mechanical problems, which should be fixed. A regular rotation guarantees that each vessel is easily subject to equivalent microwave radiation.

At the end of stage five allow the turntable to keep rotating while releasing the pressure through the pressure relief valve 1110 for a period of nine to 10 minutes. The Teflon® tubings 900 and the fluoroptic temperature probe 410 are disconnected. The liners 402 containing the asphalt samples are then placed in a convection oven at 150° C. for five minutes. The six samples are then degassed and poured into a common container. These samples are then available for use for subsequent testing of the desired parameters, e.g., stiffness, ductility, etc.

Accordingly, I have found that my method, as above described, provides asphalt samples indicative of accelerated aging (oxidation) suitable for use in subsequent conventional testing but at a foreshortened period of time compared to the conventional RTFOT and PAV methods. The use of my method introduces no new characteristics into the sample such that they simulate samples provided by the RTFOT and PAV methods. Thus, the residue may be used for subsequent analysis according to conventional testing. As such, the heretofore known methods of simulating an oxidation aging of the asphalt binders are achieved but at a reduced time period with accompanying advantages and results.

Asphalt binders aged using this method can be used to determine specification properties in accordance with AASHTO provisional standard MPI, September 1993, entitled "Standard Specification for Performance Graded Asphalt Binder" including the measurement of the intermediate temperature stiffness ($G^*.\sin \delta$), the low temperature stiffness (s), slope (m) and failure strain. These tests are also run on asphalt from the manufacturer's tank as well to determine such properties before and after aging.

It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is:

1. A method for producing an asphalt sample simulating an oxidative aging of the asphalt comprising the steps of:
   (a) accumulating a sample of the asphalt from the asphalt mass to be tested;
   (b) providing a calibrated microwave unit;

(c) placing the asphalt sample within the microwave unit;
(d) pressurizing the sample at a selected pressure of about 440 psi;
(e) monitoring the temperature of said sample;
(f) initially operating the unit for providing microwave radiation about the sample for heating the sample to a first selected temperature of approximately 27° C.;
(g) operating the unit for providing microwave radiation about the sample at a power incrementally increasing the sample temperature from said first temperature to a desired second temperature of approximately 147° C. over approximately a first 60-minute period;
(h) upon said sample reaching said second temperature operating said microwave at said second temperature for maintaining said sample at said second sample temperature for approximately a period of time of 210 minutes;
(i) releasing the pressure from said asphalt sample for returning said pressure on said sample to an ambient air pressure;
(j) placing said sample in a convection oven and heating said sample at approximately a 150° C. temperature for approximately five minutes;
(k) degassing said sample whereby to present an asphalt sample simulating an accelerated oxidative aging for subsequent analysis of selected parameters of said asphalt.

2. The method as claimed in claim 1 including the step of circulating said microwave radiation about said unit during said operating steps of said unit.

3. The method as claimed in claim 1 wherein a weight of said sample comprises approximately 11.0±1.0 grams.

4. The method as claimed in claim 1 wherein the initial power of said microwave unit operation in said step (f) is approximately at least 720 watts.

5. The method as claimed in claim 4 wherein the power of said microwave unit operation in said step (g) is approximately 850±5 watts.

6. The method as claimed in claim 5 wherein the power of said microwave unit operation in said step (h) is approximately 1050±10 watts.

7. The method as claimed in claim 1 wherein said step (a) of accumulating comprises accumulating of a plurality of discrete samples from said asphalt mass, each of said samples placed within said unit.

8. The method as claimed in claim 1 wherein said samples are initially heated to a common temperature of 150° C. for a 60-minute period by convection heating prior to said step (f).

9. The method as claimed in claim 1 wherein said sample in step (a) is placed in a vessel, said vessel previously preheated to remove moisture and cooled to room temperature.

* * * * *